United States Patent
Chandler

(10) Patent No.: US 7,260,485 B2
(45) Date of Patent: Aug. 21, 2007

(54) METHOD AND SYSTEMS FOR DISTINGUISHING BETWEEN MATERIALS HAVING SIMILAR SPECTRA

(75) Inventor: Don J. Chandler, Austin, TX (US)

(73) Assignee: Luminex Corporation, Austin, TX (US)

( * ) Notice: Subject to any disclaimer, the term of this patent is extended or adjusted under 35 U.S.C. 154(b) by 153 days.

(21) Appl. No.: 10/885,420

(22) Filed: Jul. 6, 2004

(65) Prior Publication Data

US 2005/0012034 A1    Jan. 20, 2005

Related U.S. Application Data

(60) Provisional application No. 60/488,600, filed on Jul. 18, 2003.

(51) Int. Cl.
*G06F 19/00*    (2006.01)

(52) U.S. Cl. .............. 702/28; 702/29; 702/30; 702/31; 702/70; 702/71; 702/72; 702/73; 702/74; 702/76; 702/77; 702/78; 250/339.12

(58) Field of Classification Search ............ 702/28, 702/29–31, 70–74, 76–78; 250/339.12, 461.1; 436/164; 235/491
See application file for complete search history.

(56) References Cited

U.S. PATENT DOCUMENTS

| | | | | |
|---|---|---|---|---|
| 4,717,655 A | * | 1/1988 | Fulwyler | 435/7.2 |
| 4,786,813 A | * | 11/1988 | Svanberg et al. | 250/461.1 |
| 4,849,595 A | * | 7/1989 | Fowler | 219/719 |
| 5,218,529 A | * | 6/1993 | Meyer et al. | 702/28 |
| 5,736,330 A | | 4/1998 | Fulton | |
| 5,849,595 A | * | 12/1998 | Alfano et al. | 436/164 |
| 5,981,180 A | | 11/1999 | Chandler et al. | |
| 6,046,807 A | | 4/2000 | Chandler | |
| 6,057,107 A | | 5/2000 | Fulton | |

(Continued)

OTHER PUBLICATIONS

Keij et al., "Flow Cytometric Characterization and Classification of Multiple Dual-Color Fluorescent Microspheres Using Fluorescence Lifetime," Cytometry, vol. 33, No. 3, 1998, pp. 318-323.

(Continued)

*Primary Examiner*—Marc S. Hoff
*Assistant Examiner*—Phuong Huynh
(74) *Attorney, Agent, or Firm*—Charles D. Huston; Mollie E. Lettang; Daffer McDaniel, LLP

(57) ABSTRACT

Various computer-implemented methods and systems are provided. One computer-implemented method includes determining a ratio between output signals generated by detecting spectra for a single event in two or more detection windows. The spectra are characteristic of different materials. At least a portion of the spectra overlap in at least one of the two or more detection windows. The method also includes determining which of the different materials are associated with the ratio. One embodiment of a system includes one or more detectors configured to detect spectra for a single event in two or more detection windows. The spectra may include spectra as described above. The one or more detectors are also configured to generate output signals in response to the detected spectra. The system also includes a processor configured to determine a ratio between the output signals and to determine which of the different materials are associated with the ratio.

46 Claims, 1 Drawing Sheet

U.S. PATENT DOCUMENTS

| | | |
|---|---|---|
| 6,139,800 A | 10/2000 | Chandler |
| 6,268,222 B1 | 7/2001 | Chandler et al. |
| 6,366,354 B1 | 4/2002 | Chandler |
| 6,411,904 B1 | 6/2002 | Chandler |
| 6,449,562 B1 | 9/2002 | Chandler et al. |
| 6,514,295 B1 | 2/2003 | Chandler et al. |
| 6,524,793 B1 | 2/2003 | Chandler et al. |
| 6,528,165 B2 | 3/2003 | Chandler |
| 6,549,861 B1 * | 4/2003 | Mark et al. .................. 702/76 |
| 6,592,822 B1 | 7/2003 | Chandler |
| 6,786,416 B2 * | 9/2004 | Soni et al. .................. 235/491 |

OTHER PUBLICATIONS

Vignali, "Multiplexed particle-based flow cytometric assays," Journal of Immunological Methods, vol. 243, No. 1-2, 2000, pp. 243-255.

International Search Report, Application No. PCT/US2004/022038, mailed Nov. 15, 2004.

* cited by examiner

METHOD AND SYSTEMS FOR DISTINGUISHING BETWEEN MATERIALS HAVING SIMILAR SPECTRA

PRIORITY CLAIM

This application claims priority to U.S. Provisional Application No. 60/488,600 entitled "Method for Distinguishing Between Similar Absorption or Emission Spectra," filed Jul. 18, 2003, which is incorporated by reference as if fully set forth herein.

BACKGROUND OF THE INVENTION

1. Field of the Invention

This invention generally relates to methods and systems for distinguishing between materials having similar spectra. Certain embodiments relate to a computer-implemented method that includes determining which material(s) are associated with a ratio between output signals generated by detecting spectra for a single event in two or more detection windows.

2. Description of the Related Art

Spectroscopic techniques are widely employed in the analysis of chemical and biological systems. Most often, these techniques involve the absorption or emission of electromagnetic radiation by the material of interest. In many cases, scanning the entire relevant section of the spectrum being studied is performed at a slow rate to provide the most accurate measure of absorption or emission. In other systems, however, it is only necessary to examine a specific portion of the spectrum in order to qualify or quantify the parameter under consideration. This examination may be used if, for example, the number of samples is relatively large or the samples must be analyzed relatively quickly. In such situations, the use of small spectral "snapshots" may increase sample throughput by decreasing the amount of raw data that is processed and analyzed.

One such application is in the field of microarrays, which is a technology exploited by a large number of disciplines including the combinatorial chemistry and biological assay industries. One company, Luminex Corp. of Austin, Tex., has developed a system in which biological assays are performed on the surface of variously colored fluorescent microspheres. One example of such a system is illustrated in U.S. Pat. No. 5,981,180 to Chandler et al., which is incorporated by reference as if fully set forth herein. These microspheres are interrogated in a fluid flow device by laser excitation and fluorescence detection of each individual microsphere as they pass at relatively high speed through a detection zone. Such a system is capable of analyzing thousands of microspheres a second, with each microsphere emitting several distinct, detectable signals. Obviously, taking a complete spectrum and interpreting and decoding the signals from each of the many thousands or millions of microspheres would generate an unmanageable quantity of data. The system described by Chandler et al., however, accomplishes management of the data by detecting only the fluorescence in particular "windows," which are relatively short (e.g., about 20 nm to about 40 nm), continuous portions of the overall spectral emission from the microsphere. As such, rather than generating a complete fluorescence spectrum for each microsphere, this system generates only a single value (which correlates to the intensity of the signal) for each window. These values may be easily exported to a database for further analysis.

In the above-mentioned system, fluorescent dyes are absorbed into the microspheres and/or bound to the surface of the microspheres. The dyes are chosen based on their ability to emit light in the wavelength of the chosen window. Further, the windows are spaced, and the dyes are designed to minimize, and preferably to eliminate, the overlap of a dye's fluorescent signal within adjacent windows. By employing two windows and two dyes, each at 10 different concentrations, there would thus be 100 fluorescently distinguishable microsphere sets.

Another example of an assay method is illustrated in U.S. Pat. No. 4,717,655 to Fulwyler, which is incorporated by reference as if fully set forth herein. In particular, Fulwyler describes a method of distinguishing multiple subpopulations of cells that includes labeling particles with two or more marking agents. These particles are marked in a plurality of different pre-selected ratios of the agents ranging between zero percent and one hundred percent of each agent. Each such agent has distinguishing, quantifiable marking characteristics. In other words, each fluorochrome has distinct emission and/or excitation spectra in specifically designed color bands. The differently labeled particles are mixed with cells suspected of having specific receptors for the differently labeled particles. Each cell is analyzed to determine the ratio of any two identifiable marking characteristics associated with each cell so that it can be classified in a subpopulation category if its ratio of marking characteristics is related to one of the pre-selected ratios of marking agents. Therefore, the method utilizes ratios to distinguish differently labeled particles by detecting a signal from each of two dyes.

In either system or method described above, there are several ways in which the number of distinguishable sets can be expanded. The use of a different sized microsphere, which can be distinguished on the basis of light scatter, will effectively double the number of sets. Another is to increase the number of distinguishable intensities for each dye. For example, if 15 different dye intensities were possible rather than 10 in the example case, then 225 sets would be achievable. A third method would be to add a third window, and subsequently a third dye, or even more, which would exponentially increase the number of sets. Each of these methods has been successfully tested and are being used to varying degrees. However, each adds a layer of complexity to the system, which can greatly add to the expense or difficulty of producing the platform.

SUMMARY OF THE INVENTION

The present invention generally relates to methods of distinguishing between two or more unique but similar spectra. Certain embodiments include detecting a signal in two or more different detection "windows" that are common to both or all spectra. The methods described herein may be used to distinguish between populations of particles that exhibit these different spectral characteristics and will find utility in a number of fields including clinical biological assays.

One embodiment relates to a computer-implemented method that includes determining a ratio between output signals generated by detecting spectra for a single event in two or more detection windows. As used herein, the term "event" is defined as a sample or a portion of a sample for which measurement(s) can be performed to produce output signal(s) that contain meaningful information. In the context of clinical biological assays, an event may be a microsphere, particle, or cell as it flows through a measurement window of a fluid flow optical device (e.g., a flow cytometer type instrument). Obviously, there are a number of other samples or portions of a sample that the term "event" can be used to describe, and the term "event" as used herein is intended to encompass all possible alternatives.

The term "detection window" as used herein generally refers to a wavelength or range of wavelengths at which an output signal may be generated. The wavelength or the range of wavelengths may be determined by the wavelength(s) of an illumination source used to illuminate a material and/or the wavelength(s) of light that a detector, which is configured to detect light emitted, scattered, or transmitted by the material, can detect. More commonly, however, the wavelength(s) of the detection windows will vary depending on the materials that are being distinguished between and their respective spectra. For example, the spectra are characteristic of different materials. In addition, at least a portion of the spectra overlap preferably in at least one of the two or more detection windows. The method also includes determining which of the different materials are associated with the ratio. In some embodiments, the method may also include determining a concentration of the different materials that are associated with the ratio.

In an embodiment, the two or more detection windows span different continuous portions of the overall spectra of the different materials. In addition, each of the output signals may have a single value corresponding to an intensity of the spectra detected in the corresponding detection window.

In one embodiment, the two or more detection windows include detection windows of different detectors. In an alternative embodiment, the two or more detection windows include different detection windows of one detector. In some embodiments, the spectra have peaks at approximately the same wavelength. Alternatively, the spectra may have peaks at different wavelengths. In either embodiment, one of the two or more detection windows may lie entirely within another of the two or more detection windows.

The spectra may be produced as a result of light emitted, absorbed, or transmitted by the different materials. In some embodiments, the spectra are produced as a result of fluorescence emitted by the different materials. In another embodiment, the different materials include materials associated with microspheres. In such an embodiment, the spectra may include different fluorescence emission spectra of the materials. In an additional embodiment, the different materials may include materials in solution. In such an embodiment, the spectra may include different absorption, transmittance, or emission spectra of the materials. In a further embodiment, the spectra may include a combination of spectra of two or more of the materials in solution. In this embodiment, the method may include determining individual concentrations or ratios for the two or more materials in solution. In one embodiment, the output signals may be generated by a fluid flow optical device (e.g., a flow cytometer type instrument). In other embodiments, the output signals may be generated by a spectroscopic technique. Each of the embodiments of the method described above may include any other steps described herein.

An additional embodiment relates to another computer-implemented method. This method includes determining a ratio between output signals generated by detecting spectra for a single event in two or more detection windows. The spectra are characteristic of different materials. At least a portion of the spectra overlap in at least one of the two or more detection windows. The method also includes determining concentrations of one or more of the different materials by comparing the ratio to a known ratio for a substantially pure sample of individual materials of the different materials. In one embodiment, the different materials are mixed. In another embodiment, the spectra are detected substantially simultaneously.

In one embodiment, the two or more detection windows include detection windows of different detectors. In a different embodiment, the two or more detection windows include different detection windows of one detector. The two or more detection windows span different continuous portions of the overall spectra of the different materials. In some embodiments, the spectra have peaks at approximately the same wavelength. In other embodiments, the spectra have peaks at different wavelengths. In an additional embodiment, one of the two or more detection windows may lie entirely within another of the two or more detection windows.

In an embodiment, the spectra are produced as a result of fluorescence emitted by the different materials. Alternatively, the spectra may be produced as a result of light emitted, absorbed, or transmitted by the different materials. In one embodiment, the different materials include materials associated with microspheres, and the spectra include different fluorescence emission spectra of the materials. In another embodiment, the different materials may include materials in solution, and the spectra may include different absorption, transmittance, or emission spectra of the materials.

In some embodiments, each of the output signals has a single value corresponding to an intensity of the spectra detected in the corresponding detection window. In one embodiment, the output signals are generated by a fluid flow optical device. In a different embodiment, the output signals are generated by a spectroscopic technique. Each of the embodiments of the method described above may include any other steps described herein.

Another embodiment relates to a different computer-implemented method that includes determining a ratio between output signals generated by detecting spectra for a single event in two or more detection windows. At least a portion of the spectra overlap in at least one of the two or more detection windows. The method also includes distinguishing between the spectra from the ratio. The method may also include any other steps described herein.

The methods described herein advantageously provide accurate ways for two or more different, but similar, spectra to be distinguished from each other. Therefore, the methods may also be used to distinguish between different materials that have similar spectra as described above. As such, the methods increase the number of dye materials that can be used in a measurement method since dye materials that have similar spectra may be distinguished from one another using the methods described herein. Additional advantages of the methods and systems described herein will be evident upon reading the detailed description provided below.

An additional embodiment relates to a system that includes one or more detectors and a processor. The one or more detectors are configured to detect spectra for a single event in two or more detection windows. The spectra are characteristic of different materials. At least a portion of the spectra overlap in at least one of the two or more detection windows. The one or more detectors are also configured to generate output signals in response to the detected spectra. The processor is configured to determine a ratio between the output signals. The processor is also configured to determine which of the different materials are associated with the ratio.

In one embodiment, the processor is further configured to determine a concentration of the different materials that are associated with the ratio.

The two or more detection windows span different continuous portions of the overall spectra of the different materials. In one embodiment, one of the two or more detection windows lies entirely within another of the two or more detection windows. In addition, each of the output signals may have a single value corresponding to an intensity of the spectra detected in the corresponding detection window.

In one embodiment, the two or more detection windows may include detection windows of different detectors. In another embodiment, the two or more detection windows include different detection windows of one detector. In some embodiments, the spectra have peaks at approximately the same wavelength. In other embodiments, the spectra have peaks at different wavelengths.

The spectra are produced as a result of light emitted, absorbed, or transmitted by the different materials. In one embodiment, the spectra are produced as a result of fluorescence emitted by the different materials. In another embodiment, the different materials include materials associated with microspheres. In one such embodiment, the spectra include different fluorescence emission spectra of the materials. In one embodiment, the system is configured as a fluid flow optical device. In another embodiment, the system is configured to perform a spectroscopic technique. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
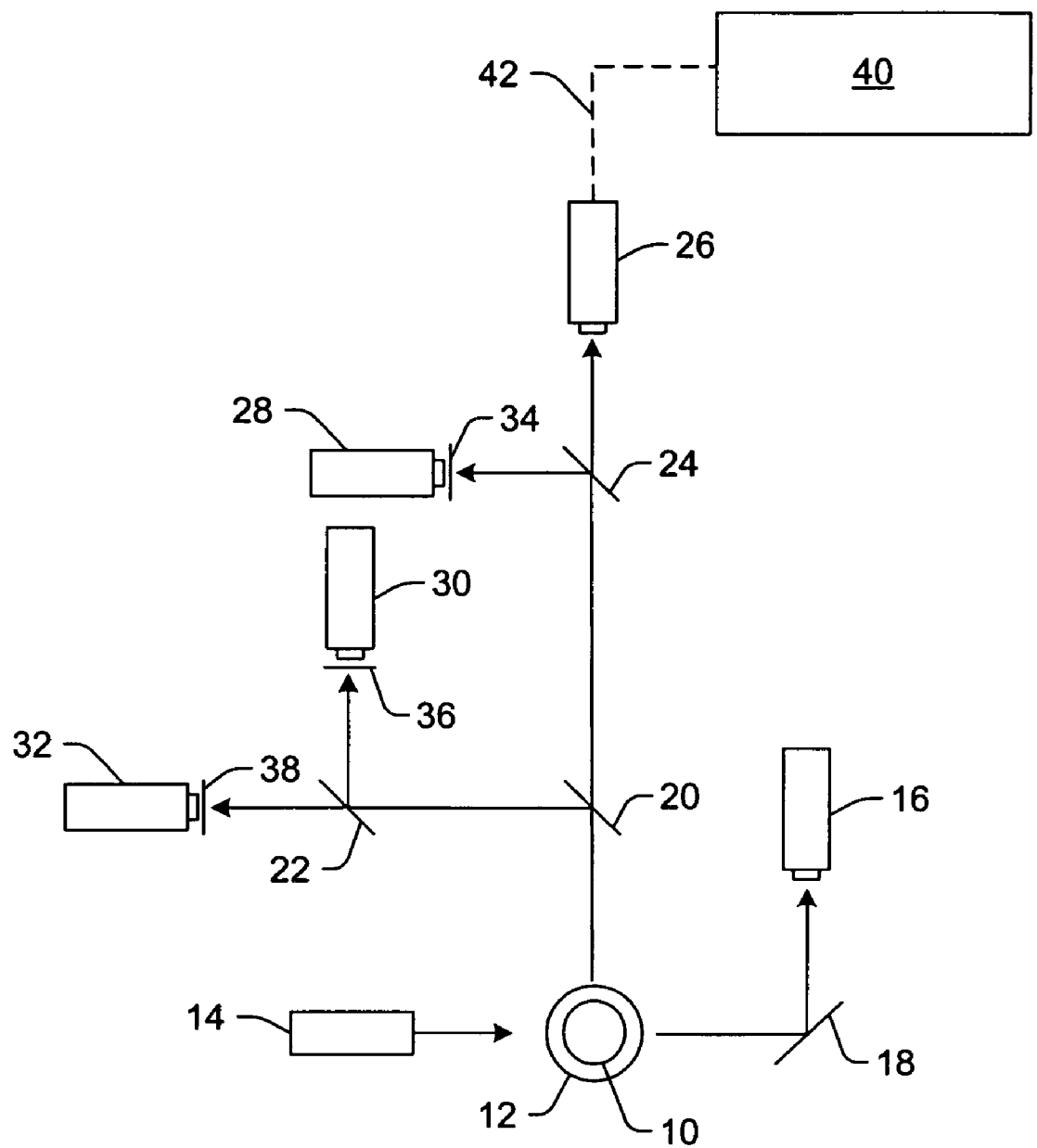
FIG. 1 is a schematic diagram illustrating one example of a system that may be used to carry out the methods described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

It is noted that the following description describes generally a technique to interpret spectra. The following description will generally use fluorescence and fluorescent microspheres in a fluid flow optical device as examples of the application of the concept. However, the examples provided herein are not intended to limit the use of this technique. For example, it will be obvious to those skilled in the art that this is a general spectroscopic technique not limited to fluorescence, particles, or fluid flow devices. Examples of appropriate microspheres, beads, and particles are illustrated in U.S. Pat. No. 5,736,330 to Fulton, U.S. Pat. No. 5,981,180 to Chandler et al., U.S. Pat. No. 6,057,107 to Fulton, U.S. Pat. No. 6,268,222 B1 to Chandler et al., U.S. Pat. No. 6,449,562 B1 to Chandler et al., U.S. Pat. No. 6,514,295 B1 to Chandler et al., U.S. Pat. No. 6,524,793 B1 to Chandler et al., and U.S. Pat. No. 6,528,165 B2 to Chandler, which are incorporated by reference as if fully set forth herein. The methods described herein may be used with any of the microspheres, beads, and particles described in these patents. In addition, microspheres for use in flow cytometry may be obtained from manufacturers such as Luminex Corp., Austin, Tex.

Other spectroscopic techniques where the measured parameter shows a reproducible distribution over a range can also be used such as infrared, ultraviolet/visible (UV/Vis), Raman, nuclear magnetic resonance (NMR), radioactive emissions, etc. Also, the detectable parameter may be emission, absorption, transmittance, etc. Detection of the signal may be accomplished by any appropriate device including, but not limited to, photo-multiplier tubes, avalanche photodiodes, charge coupled devices, pin diodes, etc. In addition to particles, the medium may be a solid, liquid, gas, or any other form where signal types as described herein can be observed.

In traditional spectroscopy, such as fluorescence spectroscopy for example, the wavelength of the source or the detector is varied over a range of wavelengths to produce a continuous spectrum for the material being examined. An alternative, when the characteristics of the material are known, but it is desired to detect its presence or concentration, is to hold the excitation and detection wavelengths constant and record the resultant signals. This procedure produces a single value for the signal that is attributable to those specific conditions. The weakness of this analytical method, however, is that a similar material may also show a signal in the spectral "window" being monitored even though its full spectrum is demonstrably different.

An example of signals that may be similar in a spectral window would be the fluorescent signals emitted by Rhodamine B and Rhodamine 6G. The former has a peak emission at 543 nm and the latter at 524 nm. If the detection window is set to monitor the spectral region from 520 nm to 550 nm, both of these dyes will show a significant signal when excited at the appropriate wavelength. If it is known which dye is being observed, it is possible to determine the concentration of dye in the solution based on the observed signal. However, if it is not known which dye is in the system, this signal will not provide a method of distinguishing between them. More spectral information is required to make this distinction.

The use of an additional detection window will allow the distinction between two similar spectra. As described above, detection windows span different continuous portions of the overall spectra of the different materials. However, unlike previous methods and systems, in the methods and systems described herein, the spectra of multiple materials overlap in at least one of the two or more detection windows. For example, in reference back to the above example, the addition of a detection window configured to detect spectra from about 550 nm to about 560 nm would provide sufficient information to distinguish between the dyes, and thus allow determination of concentration. Since each dye emits a broad signal, each will have a portion of that signal in this new window. Calculating the ratio, R, of the signals of the second window (550 nm to 560 nm) to the first window (520 nm to 550 nm) will show that R for Rhodamine B will be greater than R for Rhodamine 6G. Importantly, the ratio observed for a particular dye will be somewhat constant over a wide range of dye concentrations. The usefulness of this technique requires that the spectra of the dyes be different enough that the observed ratios can be consistently distinguished over the operating range of concentrations.

In general, therefore, at least a portion of spectra, which are characteristic of different materials, preferably overlap in at least one of two or more detection windows. Output signals for the detection windows may have a single value corresponding to an intensity of the spectra detected in the corresponding detection window. In this manner, a ratio between the output signals generated by detecting spectra for a single event in the two or more detection windows can be used to determine which of the different materials are associated with the ratio. The output signals may be generated by a fluid flow optical device such as the system described herein. Alternatively, the output signals may be generated by a spectroscopic technique including any such technique known in the art.

In addition, it is important to note that this system is not limited to distinguishing between only two dyes (or other absorbing or emitting materials). The number of dyes distinguishable by a set of two windows can be expanded by optimization of window location and width, along with judicious choice of dyes. The ability to generate a unique ratio between the observed signals provides for discerning different spectral emissions. Also, the signal from a window may be zero for one dye, as long as the other dye has a signal of greater than zero in this window since each dye would generate a unique ratio. Similarly, the methods described herein are not limited to only two signal detection windows. Improved spectral discrimination may be achieved through the use of additional windows although the additional windows will increase the quantity of data that is manipulated. In addition, the size of the detection windows may be substantially different from those given as examples. For example, the size of the detection windows is only limited by the efficiency of the detection system to define the range and reproducibly measure a signal in that range.

It is also significant to note that the two or more spectra may or may not be offset with regard to their peaks (e.g., peak intensities). If, for example, the emission spectra of two fluorescent dyes show a peak at approximately the same wavelength, but the width of one of the peaks is greater than the other, then these differences in the spectra may result in a unique ratio of intensities between the signals in the two detection windows. In these and other embodiments, one of the two or more detection windows may or may not lie entirely within another of the two or more detection windows.

A further example illustrates an application of the methods described herein. In the case of the aforementioned fluorescently dyed microspheres, 100 spectrally distinct sets of microspheres can be generated by dyeing the populations of microspheres with two different fluorescent dyes (here designated A and B) that have minimal spectral overlap. One such example is illustrated in U.S. Pat. No. 6,514,295 to Chandler et al., which is incorporated by reference as if fully set forth herein. If dye solutions are prepared with 10 different concentrations of each of the two dyes, then 100 distinct dyeing solutions and 100 fluorescently distinct microsphere populations may be produced. These unique microspheres may be spectrally distinguished using a flow cytometer or other devices capable of spectrally interrogating individual microspheres, or groups of microspheres.

The microspheres may be spectrally distinguished by detecting the emission signal in a narrow wavelength band window (e.g., in two windows, designated herein as window 1 and window 2). Further, window 1 is selected to efficiently detect the signal from dye A, and window 2 is selected to correspond with the emission from dye B. If a third window is added (i.e., window 3), which is spectrally close to window 2, then a third dye (dye B') can be selected that will also emit a signal detectable by windows 2 and 3, and result in a unique ratio between windows 2 and 3. Then, by creating 100 new dye solutions utilizing 10 different concentrations each of dyes A and B', 100 new fluorescent microsphere populations may be created. It can be easily seen that the addition of another dye (dye B"), which is able to generate a unique ratio between the signals from windows 2 and 3, will allow an additional 100 unique bead populations to be constructed using dyes A and B". Additional populations can be generated in a similar manner providing that dyes can be found that will generate a unique ratio. Further, if another window is added (window 4), which is spectrally close to window 1, then a similar series can be constructed using new dyes (dye A', A", etc.) combined with dyes B, B', B", etc., to greatly expand the potential number of unique fluorescent microsphere sets.

In another embodiment, the methods can be used to deconvolute overlapping spectra that are determined substantially simultaneously, such as may be seen when a mixture of compounds are present. For example, materials that are attached to microspheres can be distinguished as described above. In one such embodiment, the method may include determining concentrations of one or more of the different materials by comparing the ratio to a known ratio for a substantially pure sample of individual materials that are suspected to make up the different materials. However, the concentrations may be determined from the ratio using any other method known in the art. In this manner, the method may be used to identify microspheres in a multi-reporter assay that uses two or more dyes on the surface of a bead where the determined concentrations of the dyes are used to determine microsphere identity. Such materials may also include, for example, fluorescent agents attached in some way to nucleic acids, enzymes, antigens, etc. Another example would be a solution of two or more dyes, where it is desired to detect or determine the concentration or concentration ratios of each dye. In particular, the spectra may include spectra of different materials in solution. In such an embodiment, the spectra may include different absorption, transmittance, or emission spectra of the materials. In addition, the spectra may include a combination of the spectra of the two or more materials in the solution. The method may also include determining individual concentrations or ratios for the two or more materials in solution.

In such examples, as described above, using fluorescent dyes as an example, if dye A by itself generates a ratio of 1 between the two detection windows, and dye B by itself generates a ratio of 100, then a mixture of the two dyes will generate a ratio of between 1 and 100. Further, if the mixture is predominately composed of dye A, the observed ratio will be closer to 1 while if there is more of dye B, the ratio will be closer to 100. Therefore, the ratio will correlate to the composition of the dye mixture, so that for a particular ratio it would be possible to calculate the proportion of the observed signal that is due to the contribution of each dye. It follows that when the portion of the signal that is attributable to each dye is known, and the correlation of signal to dye concentration is known, then the concentrations of the two dyes can be determined simultaneously. Complications may arise from interactions between dyes such as quenching and other energy transfer phenomena, but these can be accounted for by construction of a standard curve using known combinations of dye concentrations. The complexity of analyzing the spectrum of a mixture of three or more overlapping dyes may increase markedly, possibly giving rise to several potential solutions. However, it may be possible to eliminate the incorrect solutions through other means.

FIG. 1 illustrates one example of a measurement system that may be used to perform the methods described herein. It is noted that FIG. 1 is not drawn to scale. In particular, the scale of some of the elements of the figure are greatly exaggerated to emphasize characteristics of the elements.

In FIG. 1, the measurement system is shown along a plane through the cross-section of cuvette 12 through which microspheres 10 flow. In one example, the cuvette may be a standard quartz cuvette such as that used in standard flow cytometers. Any other suitable type of viewing or delivery chamber, however, may also be used to deliver the sample for analysis. The measurement system includes light source 14. Light source 14 may include any appropriate light source known in the art such as a laser. The light source may be configured to emit light having one or more wavelengths such as blue light or green light. Light source 14 may be configured to illuminate the microspheres as they flow through the cuvette. The illumination may cause the microspheres to emit fluorescent light having one or more wavelengths or wavelength bands. In some embodiments, the system may include one or more lenses (not shown) configured to focus light from the light source onto the microspheres or the flowpath. The system may also include more than one light source. In one embodiment, the light sources may be configured to illuminate the microspheres with light having different wavelengths (e.g., blue light and green light). In some embodiments, the light sources may be configured to illuminate the microspheres at different directions.

Light scattered forwardly from the microspheres may be directed to detection system 16 by folding mirror 18 or another light directing component. Alternatively, detection system 16 may be placed directly in the path of the forwardly scattered light. In this manner, the folding mirror or other light directing component(s) may not be included in the system. In one embodiment, the forwardly scattered light may be light scattered by the microspheres at an angle of about 180 degrees from the direction of illumination by light source 14, as shown in FIG. 1. The angle of the forwardly scattered light may not be exactly 180 degrees from the direction of illumination by the light source such that incident light from the light source may not impinge upon the photosensitive surface of the detection system. For example, the forwardly scattered light may be light scattered by the microspheres at angles less than or greater than 180 degrees from the direction of illumination (e.g., light scattered at an angle of about 170 degrees, about 175 degrees, about 185 degrees, or about 190 degrees).

Light scattered and/or emitted by the microspheres at an angle of about 90 degrees from the direction of illumination by the light source may also be collected. In one embodiment, this scattered light may be separated into more than one beam of light by one or more beamsplitters or dichroic mirrors. For example, light scattered at an angle of about 90 degrees to the direction of illumination may be separated into two different beams of light by beamsplitter 20. The two different beams of light may be separated again by beamsplitters 22 and 24 to produce four different beams of light. Each of the beams of light may be directed to a different detection system, which may include one or more detectors. For example, one of the four beams of light may be directed to detection system 26. Detection system 26 may be configured to detect light scattered by the micro spheres.

The other three beams of light may be directed to detection systems 28, 30, and 32. Detection systems 28, 30, and 32 may be configured to detect fluorescence emitted by the microspheres. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence. In another example, different detectors may have different detection windows, in at least one of which, as described further above, at least a portion of the spectra of different materials overlap. In a different example, one of the detectors may have different detection windows, in one of which at least a portion of the spectra of different materials overlap. One example of a detector that may have multiple detection windows is a multi-anode photomultiplier tube, in which each anode may used as a different detection window.

In some embodiments, spectral filters 34, 36, and 38 may be coupled to detection systems 28, 30, and 32, respectively. The spectral filters may be configured to block fluorescence of wavelengths other than that which the detection systems are configured to detect. In addition, one or more lenses (not shown) may be optically coupled to each of the detection systems. The lenses may be configured to focus the scattered light or emitted fluorescence onto a photosensitive surface of the detectors.

The detector's output current is proportional to the fluorescent light impinging on it and results in a current pulse. The current pulse may be converted to a voltage pulse, low pass filtered, and then digitized by an A/D converter (not shown). Processor 40 such as a DSP integrates the area under the pulse to provide a number which represents the magnitude of the fluorescence. In addition, the processor may perform additional functions described herein (e.g., determining a ratio between the output signals and determining which of the different materials are associated with the ratio). As shown in FIG. 1, processor 40 may be coupled to detector 26 via transmission medium 42. Processor 40 may also be coupled to detector 26 indirectly via transmission medium 42 and one or more other components (not shown) such as the A/D converter. The processor may be coupled to other detectors of the system in a similar manner.

In some embodiments, the output signals generated from fluorescence emitted by the microspheres may be processed to determine an identity of the microspheres and information about a reaction taking place on the surface of the microspheres. For example, the output signals from two of the detectors may be used to determine an identity of the microspheres, and the other output signals may be used to determine a reaction taking place on the surface of the microspheres. The identity of the microspheres may be determined based on a ratio of the output signals generated in two or more different detection windows. For example, if detection systems 30 and 32 have different detection windows, the identity of the microspheres may be determined from a ratio of output signals generated by detection system 30 to output signals generated by detection system 32, coupled with the intensity of each signal. Therefore, the selection of the detectors and the spectral filters may vary depending on the type of dyes incorporated into or bound to the microspheres and/or the reaction being measured (i.e., the dye(s) incorporated into or bound to the reactants involved in the reaction).

In one particular example, the selection of the detectors and/or the spectral filters may depend on the peak emission of dyes incorporated into or bound to the microspheres. For example, as described above, Rhodamine B has a peak emission at 543 nm, and Rhodamine 6G has a peak emission at 524 nm. If the microspheres are dyed with one or both of these dyes in various concentrations, detection system 30 may be configured to detect light in a wavelength range of about 520 nm to about 550 nm. In addition, detection system 32 may be configured to detect light in a wavelength range of about 550 nm to about 560 nm.

In another example, as described above, the emission spectra of two fluorescent dyes may not be offset, but instead may show peak emissions at approximately the same wavelength. In such an example, the characteristics of the emission spectra on either one or both sides of the peak emissions may be different. As such, the emission spectra may have a unique ratio of intensities between the signals in two detection windows. In one embodiment, therefore, although detection systems 30 and 32 may have different detection windows, the detection window of one of the detection systems may lie entirely or partially within the detection window of the other detection system. For example, if the peak emissions of two dyes are at about 540 nm, then the detection window of detection system 30 may have a wavelength range of about 530 nm to about 550 nm, and the detection window of detection system 32 may have a wavelength range of about 510 nm to about 570 nm. It is noted that the above wavelength ranges are merely examples and will vary depending upon, for example, the dyes of the microspheres.

Although the system of FIG. 1 is shown to include two detection systems having two different detection windows for distinguishing between microspheres having different dye characteristics, it is to be understood that the system may include more than two such detection windows (i.e., 3 detection windows, 4 detection windows, etc.). In such embodiments, the system may include additional beamsplitters and additional detection systems having other detection windows. The detection windows for more than two detection systems may be determined as described above. In addition, spectral filters and/or lenses may be coupled to each of the additional detection systems.

In another embodiment, the system may include two or more detection systems configured to distinguish between different materials that are reacted on the surface of the microspheres. The different reactant materials may have dye characteristics that are different than the dye characteristics of the microspheres. However, the reactant materials may have dye characteristics such that they have emission spectra that are similar. For example, the emission spectra of the reactant materials may overlap. In one embodiment, the emission spectra may have offset peak emissions but may also show a strong signal at one or more of the same wavelengths. In a different embodiment, the emission spectra may have approximately the same peak emissions but different characteristics on either one or both sides of the peak emissions. Therefore, the emission spectra and the reactant materials may be distinguished as described above.

Additional examples of measurement systems that may be used to perform the methods described herein are illustrated in U.S. Pat. No. 5,981,180 to Chandler et al., U.S. Pat. No. 6,046,807 to Chandler, U.S. Pat. No. 6,139,800 to Chandler, U.S. Pat. No. 6,366,354 to Chandler, U.S. Pat. No. 6,411,904 to Chandler, U.S. Pat. No. 6,449,562 to Chandler et al., and U.S. Pat. No. 6,524,793 to Chandler et al., which are incorporated by reference as if fully set forth herein. The measurement systems described in these patents may be configured to have detection windows as described above. The measurement system described herein may also be further configured as described in these patents.

Program instructions implementing methods such as those described herein may be transmitted over or stored on the carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

In an embodiment, a processor such as processor 40 of FIG. 1 may be configured to execute the program instructions to perform a computer-implemented method according to the above embodiments. The processor may take various forms, including a DSP, personal computer system, mainframe computer system, workstation, network appliance, Internet appliance, personal digital assistant ("PDA"), television system or other device. In general, the term "computer system" may be broadly defined to encompass any device having one or more processors, which executes instructions from a memory medium.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

It will be appreciated to those skilled in the art having the benefit of this disclosure that this invention is believed to provide methods for distinguishing between similar absorption, transmission, or emission spectra. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for determining an identity of a material, comprising:
   determining a ratio between output signals generated by detecting spectra for a single event in two or more detection windows, wherein the spectra are characteristic of different materials, and wherein at least a portion of the spectra overlap in at least one of the two or more detection windows;
   determining which of the different materials are associated with the ratio and
   outputting an identity of the material associated with the ratio to a display, database, computer or storage device.

2. The method of claim 1, wherein the two or more detection windows comprise detection windows of different detectors.

3. The method of claim 1, wherein the two or more detection windows comprise different detection windows of one detector.

4. The method of claim 1, wherein the spectra have peaks at approximately the same wavelength.

5. The method of claim 1, wherein the spectra have peaks at different wavelengths.

6. The method of claim 1, wherein the spectra are produced as a result of fluorescence emitted by the different materials.

7. The method of claim 1, wherein the two or more detection windows span different continuous portions of the overall spectra of the different materials.

8. The method of claim 1, wherein each of the output signals has a single value corresponding to an intensity of the spectra detected in the corresponding detection window.

9. The method of claim 1, wherein one of the two or more detection windows lies entirely within another of the two or more detection windows.

10. The method of claim 1, wherein the different materials comprise materials associated with microspheres, and wherein the spectra comprise different fluorescence emission spectra of the materials.

11. The method of claim 1, wherein the different materials comprise materials in solution, and wherein the spectra comprise different absorption, transmittance, or emission spectra of the materials.

12. The method of claim 11, wherein the spectra comprise a combination of spectra of two or more of the materials in solution, the method further comprising determining individual concentrations or ratios for the two or more materials in solution.

13. The method of claim 1, wherein the output signals are generated by a fluid flow optical device.

14. The method of claim 1, wherein the output signals are generated by a spectroscopic technique.

15. The method of claim 1, wherein the spectra are produced as a result of light emitted, absorbed, or transmitted by the different materials.

16. The method of claim 1, further comprising determining a concentration of the different materials that are associated with the ratio.

17. A computer-implemented method for determining concentrations of one or more different materials, comprising:
    determining a ratio between output signals generated by detecting spectra for a single event in two or more detection windows, wherein the spectra are characteristic of different materials, and wherein at least a portion of the spectra overlap in at least one of the two or more detection windows;
    determining concentrations of one or more of the different materials by comparing the ratio to a known ratio for a substantially pure sample of individual materials of the different materials; and
    outputting the concentrations of the one or more different materials to a display, database, computer or storage device.

18. The method of claim 17, wherein the different materials are mixed.

19. The method of claim 17, wherein the spectra are detected substantially simultaneously.

20. The method of claim 17, wherein the two or more detection windows comprise detection windows of different detectors.

21. The method of claim 17, wherein the two or more detection windows comprise different detection windows of one detector.

22. The method of claim 17, wherein the spectra have peaks at approximately the same wavelength.

23. The method of claim 17, wherein the spectra have peaks at different wavelengths.

24. The method of claim 17, wherein the spectra are produced as a result of fluorescence emitted by the different materials.

25. The method of claim 17, wherein the two or more detection windows span different continuous portions of the overall spectra of the different materials.

26. The method of claim 17, wherein each of the output signals has a single value corresponding to an intensity of the spectra detected in the corresponding detection window.

27. The method of claim 17, wherein one of the two or more detection windows lies entirely within another of the two or more detection windows.

28. The method of claim 17, wherein the different materials comprise materials associated with microspheres, and wherein the spectra comprise different fluorescence emission spectra of the materials.

29. The method of claim 17, wherein the different materials comprise materials in solution, and wherein the spectra comprise different absorption, transmittance, or emission spectra of the materials.

30. The method of claim 17, wherein the output signals are generated by a fluid flow optical device.

31. The method of claim 17, wherein the output signals are generated by a spectroscopic technique.

32. The method of claim 17, wherein the spectra are produced as a result of light emitted, absorbed, or transmitted by the different materials.

33. A system, comprising:
    one or more detectors configured to detect spectra for a single event in two or more detection windows, wherein the spectra are characteristic of different materials, wherein at least a portion of the spectra overlap in at least one of the two or more detection windows, and wherein the one or more detectors are further configured to generate output signals in response to the detected spectra; and
    a processor configured to determine a ratio between the output signals and to determine which of the different materials are associated with the ratio.

34. The system of claim 33, wherein the two or more detection windows comprise detection windows of different detectors.

35. The system of claim 33, wherein the two or more detection windows comprise different detection windows of one detector.

36. The system of claim 33, wherein the spectra have peaks at approximately the same wavelength.

37. The system of claim 33, wherein the spectra have peaks at different wavelengths.

38. The system of claim 33, wherein the spectra are produced as a result of fluorescence emitted by the different materials.

39. The system of claim 33, wherein the two or more detection windows span different continuous portions of the overall spectra of the different materials.

40. The system of claim 33, wherein each of the output signals has a single value corresponding to an intensity of the spectra detected in the corresponding detection window.

41. The system of claim 33, wherein one of the two or more detection windows lies entirely within another of the two or more detection windows.

42. The system of claim 33, wherein the different materials comprise materials associated with microspheres, and wherein the spectra comprise different fluorescence emission spectra of the materials.

43. The system of claim 33, wherein the system is configured as a fluid flow optical device.

44. The system of claim 33, wherein the system is configured to perform a spectroscopic technique.

45. The system of claim 33, wherein the spectra are produced as a result of light emitted, absorbed, or transmitted by the different materials.

46. The system of claim 33, wherein the processor is further configured to determine a concentration of the different materials that are associated with the ratio.

* * * * *